United States Patent [19]

Chang et al.

[11] Patent Number: 4,835,267
[45] Date of Patent: May 30, 1989

[54] PROCESS FOR THE PREPARATION OF CEPHALOSPORIN DERIVATIVES

[75] Inventors: Moon H. Chang; Bong J. Kim; Sung K. Kim; Woan J. Kim, all of Seoul, Rep. of Korea

[73] Assignee: Korea Advanced Institute of Science and Technology, Seoul, Rep. of Korea

[21] Appl. No.: 1,875

[22] Filed: Jan. 9, 1987

[30] Foreign Application Priority Data

May 7, 1986 [KR] Rep. of Korea .................... 3550

[51] Int. Cl.$^4$ .................. C07D 501/44; A61K 31/545
[52] U.S. Cl. .................... 540/226; 540/230; 540/227
[58] Field of Search ............... 540/222, 227, 225, 226, 540/230

[56] References Cited

U.S. PATENT DOCUMENTS 4,007,168  2/1977  Coll ..................... 540/230

Primary Examiner—Nicholas S. Rizzo
Attorney, Agent, or Firm—Birch, Stewart, Kolasch & Birch

[57] ABSTRACT

The present invention relates to an improved process for producing cephalosporin derivatives of formula (I), the 3-position of which being substituted by acetoxymethyl or tetrazolylthiomethyl and the 7-acyl group of which being substituted by D-mandelic acid derivatives, which comprises simultaneously reacting the compound of formula (III) with the compound of formula (IV) in the presence of a compound of formula (II) and anamine in high yield,

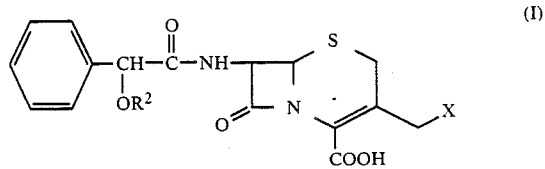

(I)

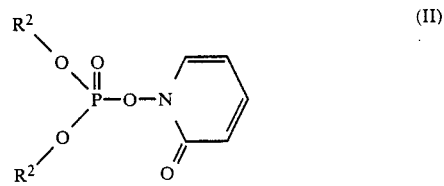

(II)

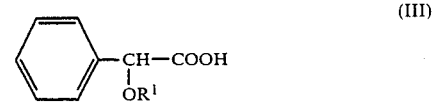

(III)

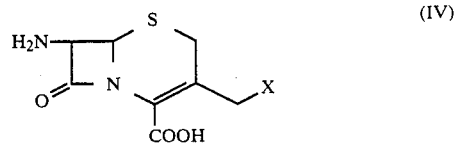

(IV)

wherein,
$R^1$ is hydrogen or

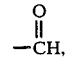

$R^2$ is methyl, ethyl, propyl or phenyl,
X is

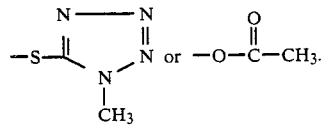

8 Claims, No Drawings

PROCESS FOR THE PREPARATION OF CEPHALOSPORIN DERIVATIVES

BACKGROUND OF THE INVENTION

The present invention relates to a new and improved process for producing cephalosporin derivatives in high yield utilizing a novel acylating agent, the 3-position of which being substituted by acetoxymethyl or tetrazolyl-thiomethyl and the 7-acyl group of which being substituted by D-mandelic acid derivatives, which is represented by the following formula (I);

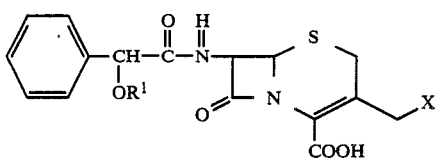   (I)

wherein X is

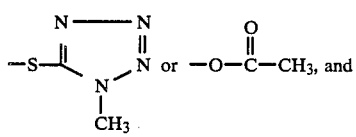

$R^1$ is hydrogen or —CHO.

The process for the preparation of the compound of formula (I), according to the present invention comprises reacting carboxylic acid of the following formula (III) with the compound of the following formula (IV) in the presence of a novel acylating agent having the following formula(II).

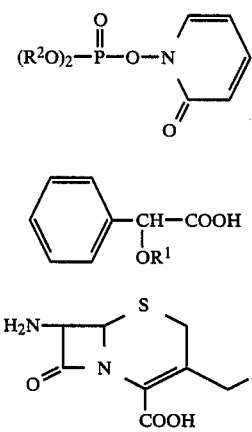

wherein, $R^2$ is methyl, ethyl, propyl, phenyl, and $R^1$ and X are the same as defined above.

The compound of formula (I) wherein X is substituted by 1-methyl-5-mercaptoteitraxole is known as an antibiotic substance, which is stable for liver enzyme as well as for cephalosporinase which is proliferated by gram-negative bacterium.

Various processes for preparing the compound of formula (I) are known in the art as examplified by Korean Patent Publication No. 75-299, U.S. Pat. Nos. 3,641,021, 3,928,592, 3,928,337, and 4,006,138 and Japanese Kokai No. 52-83,956.

Acylation processes described in the above prior art processes may be classified into two typical groups. In one process, the compound of formula (I) is produced by reacting an acid chloride which is prepared from the compound of formula (III) with the compound of formula (IV) in the presence of a halogenating agent. In other processes, the compound of the formula (I) is produced by reacting a mixed acid anhydride, which is prepared by reacting the compound of formula (III) with isobutyl chloroformate, with the compound of formula (IV) at low temperature of —20° C. to —10° C. under anhydrous condition.

However, the former prior art methods have many deficiencies since the use of a large amount of a hazardous halogenating agent and a laborious distillation process are required. Furthermore, in the latter prior art methods, there is instability in the use of the mixed acid anhydride so that it is difficult to mass produce the compound of formula (I).

OBJECTS AND SUMMARY OF THE INVENTION

Accordingly, it is therefore and object of the present invention to provide an improved process for the production of cephalosporin derivatives in high yield.

Another object of the present invention is to provide an improved process for preparing cephalosporin derivatives by utilizing an acylating agent of formula (II) under mild reaction conditions.

A further object of the present invention is to provide an improved process for the production of cephalosporin derivatives in high yield which simplifies the separation of by-products such as N-hydroxy pyridone, since it is easy for N-hydroxy pyridone to solubilize in water under acidic condition.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

The present invention relates to an improved process for producing cephalosporin derivatives of formula (I) in high yield, the 3-position of which being substituted by acetoxymethyl or tetrazolylthiomethyl and the 7-acyl group of which being substituted by D-mandelic acid derivatives, which comprises simultaneously reacting the compound of formula (IV) with the compound of formula (III) in the presence of the compound of formula (II) and an amine.

DETAILED DESCRIPTION OF THE INVENTION

The present invention provides an economical process for the production of cephalosporin derivatives, utilizing a novel acylating agent of formula (II) in the reaction between the silylated compound of formula (IV) and the compound of formula (III) in the presence of an amine.

The reaction scheme of the present invention is as follows:

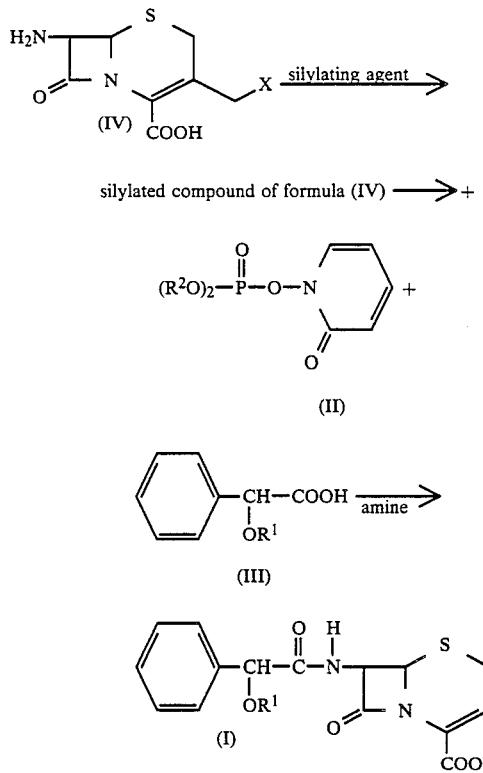

wherein R¹, R² and X are same as defined above.

The advantages related to the process, according to the present invention, in which the reaction intermediate prepared by the compounds of formulas (II) and (III) react simultaneously with the amine compound of formula (IV) without an additional separation step, is that the desired final product is obtained in a single step process. The present invention is characterized in that the compound of formula (II) which is stable, easy to handle and highly reactive can be conveniently utilized in the present process. The compound of formula (II) can be prepared by reacting 1-hydroxy-2-pyridone with dialkylchlorophosphate in the presence of a non-polar solvent and an amine, at a temperature of 0°–25° C. for about 30 min. –2 hrs. The non-polar organic solvents can include methylene chloride, chloroform, carbontetrachloride and benzene, preferably methylene chloride.

The process described above for preparing the compound of formula (I) comprises the steps of silylating the compound of formula (IV) with trimethylchlorosilane, N-(trimethylsilyl) acetamide or N,O-bis(trimethylsilyl)acetamide in the presence of organic solvent and reacting the obtained solution of the silylated compound of formula (IV) with the compound of formula (III) and the compound of formula (II) in the presence of an amine. After the reaction is completed, 1-hydroxy-2-pyridone, which is the by-product formed during the reaction, is removed selectively by washing with water under acidic conditions.

The solvents used in the present process include ethyl acetate, methylene chloride, and benzene, which are insoluble in water. The amines include triethylamine, pyridine, isopropylamine, dimethylamine, dimethylaminopyridine, etc, preferably triethylamine and pyridine.

Although the reaction temperature is generally in the range of about —50° C. to 50° C., other appropriate temperatures may be used depending upon the particular compound of formula (II). Generally, at low temperature, the reaction speed is slow and the reaction speed increases rapidly as the reaction temperature increases. The reaction period is from about 50 minutes to 2 hours.

As described above, according to the present invention, the compound of formula (III) is reacted simultaneously with the compound of formula (II) and the silylated compound of formula (IV) under mild condition to complete the process in a short period of time. Also, the by-product is conveniently removed from the final product leading to the production of the desired final product in a high yield.

The present invention is utilized in the following examples as well as in the reaction for the preparation of other cephalosporin derivatives. These examples more specifically illustrate the present invention, but should not be considered as limiting the scope thereof.

REFERENTIAL EXAMPLE 1

To 60 ml of methylene chloride is dissolved 6.2 ml of diphenyl chlorophosphate and 4.6 ml of triethylamine. The mixture is cooled to 0° C. then is added 3.33 g of N-hydroxy-2-pyridone. The solution is then stirred at 25° C. for 30 minutes to complete the reaction. The reaction solution is diluted by adding 150 ml of methylene chloride, and is successively washed with 100 ml of cold 10% HCl, 100 ml of cold saturated aqueous solution of sodium hydrogen carbonate and 100 ml of cold saturated aqueous saline. The aqueous phase is extracted with 100 ml of methylene chloride three times, and is added to organic phase and then is dried over anhyrous magnesium sulfate. Removal of the solvent by distillation under reduced pressure gives diphenyl-2-pyridone-1-yl-phosphate (9.868 g, 96%) in solid state.

IR (KBr); 1640 cm⁻¹, 1200 cm⁻¹

NMR (CDCl₃); 85.9 6.8(m,2H), 87.1 7.6(s and m, 12H)

REFERENTIAL EXAMPLE 2

To 55 ml of dried methylene chloride is added 3.21 g of N-hydroxy-2-pyridone and 4.188 ml of diethylchlorophosphate. To the mixture cooled to 5° C. is 4.17 ml of triethyl-amine over 5 minutes. The mixture is brought up to 25° and is allowed to react for 1.5 hours. The mixture which is diluted with 130 ml of methylene chloride is cooled to 5° C. and is washed successively with 100 ml of cold HCl, 100 ml of cold saturated aqueous solution of sodium hydrogen carbonate and 100 ml of saturated aqueous saline. The aqueous layers are combined, extracted with 100 ml of methylenechloride three times. Combined organic layer is dried over anhydrous magnesiumsulfate. Removal of the solvent by distillation under reduced pressure affords liquid diethyl-2-pyridone-1-yl -phosphate (u.47 g, 91%)

IR (NaBr, Film); 1640 cm⁻¹, 1210 cm⁻¹

NMR (CDCl₃); 1.32(6H,—CH₃), 4.4(4H,AB-q,—CH) 0.06–6.75(2H,m) 7.2–7.7(2H,m)

EXAMPLE 1

3.2 of 7-amino-3-(1-methyl-1H -tetrazol-5-yl-thiomethyl) -3-cephem-4-carboxylic acid and 5.20 g of monotrimethylsitly-acetamide are suspened in 90 g of ehtylacetate, brought up to 50° C., and stirred for 50 minutes to give clear solution. The reaction solution, cooled to —15°∼—20° C., to which 1.98 g of O-formyl D-mandelic acid, 4.17 g of diphenyl-2-pyridone-1-yl-phosphate thus obtained according to the referential example 1 and 1.5 g of triethylamine are successively added, is stirred for 2.5 hours at the same temperature and tested for the completion of reaction by thin layer chromatography (water; acetonitil=1:4).

When the reaction is complete, to the reaction mixture are added 100 ml of ethylacetate and 100 ml of water, and the mixture is stirred for 10 minutes, the insolubles being removed by filtration.

After the ethyacetate phase is separated, water phase is extracted twice with 100 ml of ethylacetate. Combined ethylacetate layer is successively washed twice with 100 ml of 5% nitric acid, 100 ml of saturated aqueous saline and 100 ml of saturated aqueous saline and the resulting organic phase is dried over anhydrousmagnesium sulfate.

Removal of the solvent by distillation under reduced pressure gives crude crystal, which is recrystallized from ethylacetate and n-hexane yielding 4.05 g of pure 7-(D-2-formyloxy-2-phenylacetamido)-3-(1-methyl-1H-tetrazol-5-yl-thiomethyl)-3-cephem-4-carboxylic acid.

Yield; 81.7%. IR(KBr); 1780 cm$^{-1}$

NMR (DMSO-$d_6$); 3.40(d,2H), 3.94(S,3H), 4.15(S,2H) 4.94(d,1H), 5.63(d,1H), 6.20(S,1H) 7.40(m,5H), 8.25(S,1H), 8.87(d,1H)

EXAMPLE 2

To 90 ml of ethyl acetate is suspended 3.28 g of 7-amino-3-(1-methyl-1H-tetrazol-5-yl-thiomethyl)-3-cephem-4-carboxylic acid and 5.20 g of monotrimethylsilylacetamide, and the suspension is brought up to 50° C. and is stirred for 50 minutes to give clear solution. To the solution cooled to 35° C., are successively added 1.98 g of O-formyl D-mandelic acid, 3.40 g of diethyl-2-pyridone-1-yl-phosphate thus obtained according to referential example 2 and 1.5 ml of triethylamine. The mixture is stirred for 2 hours at 35°–38° C. and then is tested for the completion of reaction by thin layer chromatography (water : acetonitril=1:4). Upon completion of the reaction, to the reaction solution cooled to 10° C. are added 100 ml of ethyl acetate, 100 ml of water and 1 ml of nitric acid. After stirring the mixture for 15 minutes, insolubles are removed by filtration, the ethylacetate phase is separated and water phase is extracted twice with 100 ml of ethylacetate.

Combined ethyl-acetate phase is successively washed twice with 100 ml of 5% nitric acid and with 100 ml of saturated aqueous saline, and the organic phase is dried over anhydrous magnesium sulfate. Removal of the solvent by distillation under reduced pressure affords crude crystal, which is recrystallized from ethylacetate and n-hexane yielding 4.30 g of pure 7-(D-2-formyloxy-2-phenylacetamido)-3-(1-methyl-1H-tetrazol-5-yl-thiomethyl)-3-cephem-4-carboxylic acid.

Yield; 88.5%, confirmed results show the same as that of example 1.

EXAMPLE 3

To 80 ml of methylenechloride is suspended 2.72 g of 7-amino-3-acetoxymethyl-3-cephem-4-carboxylic acid and 4.9 ml of N,O-bis(trimethylsilyl) acetamide, followed by stirring at ambient temperature for 2 hours to obtain clear solution. To the solution are succssively added 1.98 g of O-formyl D-mendelic acid, 4.98 g of diphenyl-2-pyridone-1-yl-phosphate and 0.80 ml of pyridine.

The mixture is stirred at 0°–5° C. for 1.5 hours to complete the reaction. To the reaction solution are added 150 ml of methylenechloride and 80 ml of water, and the water phase is extracted twice with 100 ml of methylene chloride. Combined methylenechloride phase is successively washed twice with 100 ml of 5% nitric acid and with 100 ml of saturated aqueous saline, and the organic phase is dried over anhydrous magnesiumsulfate.

Removal of the solvent by distillation under reduced pressure affords crude crystal, which is further recrystallized from ethylacetate and n-hexane to give 3.78 g (91%) fo pure 7-(D-2-formyloxy-2-phenylacetamido-3-acetoxymethyl-3-cephem-4-carboxylic acid.

IR (KBr); 1780 cm$^{-1}$

NMR (KDCl$_3$); 2.15(S,3H), 3.5(d,2H), 5.1(d,1H), 5.35 (S,3H), 6.3(S,1H), 7.40(m,5H), 8.18 (s,1H), 8,83(d,1H)

EXAMPLE 4

2.72 g of 7-amino-3-acetoxymethyl-3-cephem-4-carboxylic acid and 4.9 ml of bistrimethylsilylacetamide are suspended in 80 ml of methylene chloride and stirred at ambient temperature for 2 hours to obtain clear solution.

To the solution are successively added 1.98 g of D-mendelic acid formater ester, 3.40 g of diethyl-2-pyridone-1-yl-phosphate and 0.89 ml of pyridine, and the mixture is stirred at 35° C. for 2 hours to complete the reaction.

150 ml of methylenechloride and 80 ml of water are added to the reaction solution, and is stirred at ambient temperature for 10 minutes and methylene chloride phase is separated.

Water phase is twice extracted with 100 ml of methylenechloride Combined methylenechloride phase is washed two times with 100 ml of 5% nitric acid and with 100 ml of saturated aqueous saline, and the organic phase is dried over anhydrous magnesiumsulfate Removal of the solvent by filtration followed by distillation under reduced pressure gives crude crystal, which is further treated with ethylacetate and n-hexane yielding 3.86 g of pure 7-(D-2-formyloxy-2-phenylacetamide)-3-actoxymethyl-3-cephem-4-carboxylic acid, yield: 93%.

The analysis shows the same results as that of example 3.

EXAMPLE 5

3.28 g of 7-amino-3(1-methyl-1H-tetrazol-5-yl-thiomethyl)-3-cephem-4-carboxylic acid and 5.20 g of monotrimethylsilyacetamide are suspended in 90 ml of ethylacetate and is stirred at 50° C. for 50 minutes to give clear solution.

To the reaction solution cooled to 5° C. are successively added 1.59 g of D-mandelic acid, 4.17 g of dephenyl-2-pyridone-1-yl-phosphate and 0.89 ml of pyridine, and the mixture is stirred at 0°–5° C. for 2 hours.

100 ml of ethylacetate and 100 ml of water are added to reaction solution, stirred at ambient temperature for 10 minutes and insolubles are removed by filtration.

The ethylacetate layer is separated and the water layer is extracted three times with 100 ml of ethyl acetate.

Combined ethylacetate layer is successively washed twice with 100 ml of 5% HCl and with 100 ml of saturated aqueous saline, and the organic layer is dried over anhydrous magnesiumsulfate. removal of the solvent by filtration followed by distillation under reduced pressure affords crude crystal, which is further treated to yield 3.51 g of pure 7-(D-2-hydroxy-2- phenylacetamido)-3-(1-methyl-1H-tetrazol-5-yl-thiomethyl) -3-cephem-4-carboxylic acid.

Yield: 76%

IR (KBr): 1770 cm$^{-1}$

EXAMPLE 6

3.28 g of 7-amino-3-(1-methyl-1H-tetrazol-5-yl-thiomethyl)-3-cephem-4-carboxylacid and 5.20 g of monotrimethylsilylacetamide are suspended in 90 ml of ethylacetate and stirred at 50° for 50 minutes to give clear solution.

To the reaction solution cooled to 35° C. are added 1.59 g of D-mandelic acid, 3.40 g of diethyl-2-pyridone-1-yl -phosphate and 0.89 ml of pyridine, and is allowed to react at 35°-38 ° C. for 2.5 hours to complete the reaction.

Treatment as described in Example 5 affords 3.60 g of pure 7-(D-2-hydroxy-2-phenylacetamido)-3-(1-methyl-1H-tetrazol-5-yl-thiomethyl) -3-cephem-4-carboxylic- acid.

yield: 78%

IR (KBr): 1770 cm$^{-1}$

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing cephalosporin derivatives of formula (I) which comprises:

reacting an effective amount of a carboxylic acid of formula (III) with an effective amount of a silylated intermediate of formula (IV) in the presence of an effective amount of a novel acylating agent of formula (II) in a single step process:

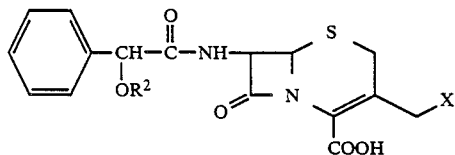

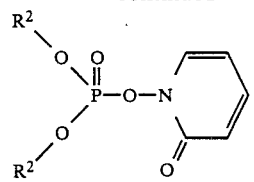

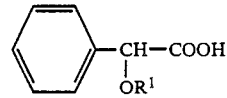

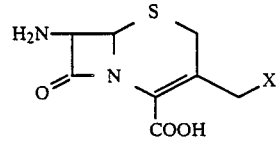

wherein, $R^1$ is hydrogen or

$R^2$ is methyl, ethyl, propyl or phenyl,

X is

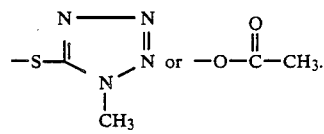

2. The process for preparing cephalosporin derivatives of claim 1 wherein the reaction is conducted in the presence of an amine and a solvent at a temperature of about —50° to 50° C.

3. The process for preparing cephalosporin derivatives of claim 2 wherein the amine is selected from the group consisting of triethylamine, pyridine, isopropylamine, dimethylamine and dimethylaminopyridine.

4. The process for preparing cephalosporin derivatives of claim 3 wherein the amine is triethylamine.

5. The process for preparing cephalosporin derivatives of claim 3 wherein the amine is pyridine.

6. The process for preparing cephalosporin derivatives of claim 2 wherein the reaction period is from about 50 minutes to 2 hours.

7. The process for preparing cephalosporin derivatives of claim 2 wherein the solvent is selected from the group consisting of ethylacetate, methylenechloride and benzene.

8. The process for preparing cephalosporin derivatives of claim 7 wherein the solvent is ethylacetate.

* * * * *